United States Patent [19]

Sugawa et al.

[11] Patent Number: 5,726,047
[45] Date of Patent: Mar. 10, 1998

[54] PROCESS FOR STEREOSELECTIVELY REDUCING 1-HALO-3-AMINO-4-PHENYL-2-BUTANONE TO THE CORRESPONDING ALCOHOL WITH MICROORGANISMS

[75] Inventors: Tadashi Sugawa, Akashi; Kenji Inoue, Kakogawa, both of Japan

[73] Assignee: Kaneka Corporation, Osaka, Japan

[21] Appl. No.: 793,134

[22] PCT Filed: Jun. 19, 1996

[86] PCT No.: PCT/JP96/01676

§ 371 Date: Apr. 4, 1997

§ 102(e) Date: Apr. 4, 1997

[87] PCT Pub. No.: WO97/00327

PCT Pub. Date: Jan. 3, 1997

[30] Foreign Application Priority Data

Jun. 19, 1995 [JP] Japan ................................ 7-176821

[51] Int. Cl.$^6$ .................................................. C12P 13/02

[52] U.S. Cl. .................. 435/129; 435/280; 435/822; 435/911

[58] Field of Search ........................ 435/129, 280, 435/822, 911

[56] References Cited

U.S. PATENT DOCUMENTS 4,857,468  8/1989  Kutsuki et al. ................ 435/280
5,266,485  11/1993  Sawa et al. ..................... 435/280

FOREIGN PATENT DOCUMENTS 63-12288  1/1988  Japan.
63-12287  1/1988  Japan.

*Primary Examiner*—Sandra E. Saucier
*Attorney, Agent, or Firm*—Pollock, Vande Sande & Priddy

[57] ABSTRACT

A process for producing optically active 1-halo-3-amino-4-phenyl-2-butanol derivatives from optically active 1-halo-3-amino-4-phenyl-2-butanone derivatives stereoselectively in a high yield by bringing the butanone derivatives into contact with microorganisms.

11 Claims, No Drawings

PROCESS FOR STEREOSELECTIVELY REDUCING 1-HALO-3-AMINO-4-PHENYL-2-BUTANONE TO THE CORRESPONDING ALCOHOL WITH MICROORGANISMS

TECHNICAL FIELD

The present invention relates to a process for producing optically active 1-halo-3-amino-4-phenyl-2-butanol derivatives and, more particularly, to an efficient process for producing optically active 1-halo-3-amino-4-phenyl-2-butanol derivatives by bringing the corresponding optically active 1-halo-3-amino-4-phenyl-2-butanone derivatives into contact with a microorganism to thereby cause stereoselective reduction of said butanone derivatives.

In particular, the present invention relates to an efficient process for producing (2S,3S)-1-halo-3-amino-4-phenyl-2-butanol derivatives by bringing the corresponding (3S)-1-halo-3-amino-4-phenyl-2-butanone derivatives into contact with a specific microorganism. Optically active 1-halo-3-amino-4-phenyl-2-butanol derivatives, in particular (2S,3S)-1-halo-3-amino-4-phenyl-2-butanol derivatives, are useful as intermediates for the production of optically active medicinal compounds such as HIV protease inhibitors, as is disclosed in Japanese Kokai Publication Hei-03-252563.

BACKGROUND ART

A process is known for the production of (2S,3S)-1-halo-3-amino-4-phenyl-2-butanol derivatives which comprises reducing chemically amino-protected (3S)-1-halo-3-amino-4-phenyl-2-butanone derivatives with a reducing agent such as sodium borohydride (Japanese Kokai Publication Hei-02-42048; Tetrahedoron, 50, 6333, 1994). However, no reports have so far dealt with a process for producing (2S,3S)-1-halo-3-amino-4-phenyl-2-butanol derivatives by causing a microorganism to act on (3S)-1-halo-3-amino-4-phenyl-2-butanone derivatives.

The above-mentioned process comprising reducing amino-protected (3S)-1-halo-3-amino-4-phenyl-2-butanone derivatives with a reducing agent such as sodium borohydride requires the use of such a relatively expensive reducing agent and, moreover, is unsatisfactory from the stereoselectivity viewpoint.

SUMMARY OF THE INVENTION

In view of the foregoing, the present invention has for its object to provide a process of reducing optically active 1-halo-3-amino-4-phenyl-2-butanone derivatives to the corresponding optically active 1-halo-3-amino-4-phenyl-2-butanol derivatives stereoselectively with good yields.

The gist of the present invention consists in that optically active 1-halo-3-amino-4-phenyl-2-butanol derivatives are produced by bringing an optically active 1-halo-3-amino-4-phenyl-2-butanone derivative of the general formula (1);

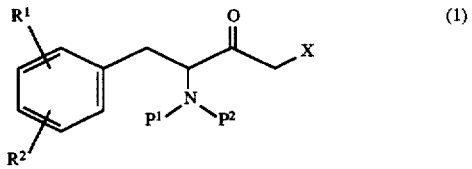

(wherein X represents a halogen atom, $R^1$ and $R^2$ each independently represents a hydrogen atom, a hydroxyl group which is optionally protected, an alkoxyl group, an alkyl group, a nitro group, an amino group which is optionally protected, or a cyano group. $P^1$ and $P^2$ each independently represents a hydrogen atom or an amino-protecting group or $P^1$ and $P^2$ combinedly represent a phthaloyl group, with the exception of the case in which both $P^1$ and $P^2$ are simultaneously hydrogen atoms.) into contact with at least one microorganism selected from the group consisting of microorganisms belonging to the genera Candida, Geotrichum, Metschnikowia, Pachysolen, Pichia, Rhodotorula, Trichosporon, Zygosaccharomyces, Botryoascus, Cryptococcus, Citeromyces, Debaryomyces, Williopsis, Kloeckera, Lipomyces, Rhodosporidium, Saccharomycopsis and Wingea and capable of stereoselectively reducing said butanone derivative to the corresponding optically active 1-halo-3-amino-4-phenyl-2-butanol derivative of the general formula (2);

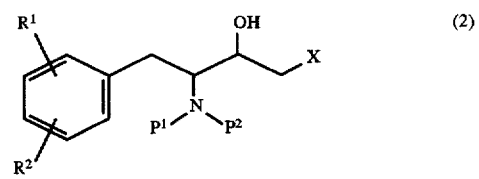

(wherein X, $R^1$, $R^2$, $P^1$ and $P^2$ are as defined above.) and recovering the resulting optically active 1-halo-3-amino-4-phenyl-2-butanol derivative.

DETAILED DISCLOSURE OF THE INVENTION

In the following, the present invention is described in further detail.

The combinations of the substituents X, $R^1$, $R^2$, $P^1$ and $P^2$ in the (3S)-1-halo-3-amino-4-phenyl-2-butanone derivatives among the optically active 1-halo-3-amino-4-phenyl-2-butanone derivatives of the above general formula (1) to be used as the substrates in the production process according to the present invention are, for example, as follows.

X is, for example, a chlorine, bromine or fluorine atom, and the chlorine atom is preferred among others.

As $R^1$ and $R^2$, there may be mentioned a hydrogen atom, a methyl group, a hydroxyl group, a methoxyl group, an amino group, etc.

As $P^1$ and $P^2$, there may be mentioned a hydrogen atom and an amino-protecting group. The amino-protecting group is not limited to any particular species but includes those protective groups generally used in protecting an amino group, for example methoxycarbonyl, t-butoxycarbonyl, benzyloxycarbonyl, ethoxycarbonyl, acetyl, trifluoroacetyl, benzyl, dibenzyl, phthaloyl, tosyl, benzoyl and the like, as described by Theodora W. Green, in Protective Groups in Organic Synthesis, second edition, John Wiley & Sons, 1990, pages 309 to 384. Among such, methoxycarbonyl, t-butoxycarbonyl, benzyloxycarbonyl, phthaloyl and the like are preferred, and methoxycarbonyl and t-butoxycarbonyl are more preferred.

The above-mentioned optically active 1-halo-3-amino-4-phenyl-2-butanone derivatives can be prepared by the methods disclosed in Japanese Kokai Publication Sho-62-126158 and Japanese Kokai Publication Hei-02-42048.

The microorganisms which are to be used in the practice of the present invention and are capable of stereoselectively and asymmetrically reducing an amino-protected (3S)-1-halo-3-amino-4-phenyl-2-butanone derivative to the corresponding (2S,3S)-1-halo-3-amino-4-phenyl-2-butanol derivative can be found out, for example, in the following manner.

In cases where a (3S)-1-halo-3-methoxycarbonylamino-4-phenyl-2-butanone is used as the optically active 1-halo- 3-amino-4-phenyl-2-butanone derivative, 5 ml of a medium (medium ①) having the composition: 40 g of glucose, 3 g of yeast extract, 6.5 g of $(NH_4)_2HPO_4$, 1.0 g of $KH_2PO_4$, 0.8 g of $MgSO_4.7H_2O$, 60 mg of $ZnSO_4.7H_2O$, 90 mg of $FeSO_4.7H_2O$, 5 mg of $CuSO_4.5H_2O$, 10 mg of $MnSO_4.4H_2O$ and 0.1 g of NaCl (per liter) is placed in a test tube, sterilized and then inoculated with the test microorganism, followed by 2 to 3 days of shake culture at 30° C. (a seed culture).

In a 500-ml Sakaguchi flask are placed 27 ml of a medium (medium ②) having the composition: 3 g of yeast extract, 6.5 g of $(NH_4)_2HPO_4$, 1.0 g of $KH_2PO_4$, 0.8 g of $MgSO_4.7H_2O$, 60 mg of $ZnSO_4.7H_2O$, 90 mg of $FeSO_4.7H_2O$, 5 mg of $CuSO_4.5H_2O$, 10 mg of $MnSO_4.4H_2O$, 0.1 g of NaCl and 5 g of $CaCO_3$ (per 900 ml) and one drop of Adekanol, followed by sterilization. After addition thereto of 3 ml of 40% glucose sterilized beforehand, 0.6 ml of the seed culture mentioned above is added and shake culture is carried out at 30° C. for 2 to 3 days.

After adjusting to pH 6 with an aqueous sodium hydroxide or sulfuric acid solution, 10 ml of this culture is shaken with 10 mg of (3S)-1-chloro-3-methoxycarbonylamino-4-phenyl-2-butanone and 400 mg of glucose in a 500-ml Sakaguchi flask at 30° C. for 1 day. The reaction mixture is extracted with methanol in a 50-ml volumetric flask and, after addition of methanol to the marked line, the product (3S)-1-chloro-3-methoxycarbonylamino-4-phenyl-2-butanol is assayed by high-performance liquid chromatography (column: Nomura Kagaku's Develosil HG3, 150 mm×φ4.6 mm; eluent: methanol/water=4/6; column temperature 40° C.; flow rate: 0.8 ml/min.; detection at 210 nm). The (2S,3S)-form is eluted at a retention time of 11.8 minutes, the (2R,3S)-form at a retention time of 16.8 minutes and the starting material (3S)-1-chloro-3-methoxycarbonylamino-4-phenyl-2-butanone at a retention time of 16.3 minutes. The optical purity and conversion rate can thus be determined.

In the practice of the present invention, any microorganism can be used if it is capable of asymmetrically converting an amino-protected optically active 1-halo-3-amino-4-phenyl-2-butanone derivative to the corresponding optically active 1-halo-3-amino-4-phenyl-2-butanol derivative with high stereoselectivity.

For instance, as such microorganism suited for asymmetric reduction of an amino-protected (3S)-1-halo-3-amino-4-phenyl-2-butanone to the corresponding (2S,3S)-1-halo-3-amino-4-phenyl-2-butanol derivative, there may be mentioned at least one microorganism selected from the group consisting of microorganisms belonging to the genera Candida, Geotrichum, Metschnikowia, Pachysolene, Pichia, Rhodotorula, Trichosporon and Botryoascus, among others.

Preferred as the above-mentioned microorganisms are, for example, *Candida etchellsii, Candida gropengiesseri, Candida halophila, Candida lactis-condensi, Candida mannitofaciens, Candida nodaensis, Candida parapsilosis, Candida sorbophila, Candida tropicalis, Candida versatilis, Geotrichum candidum, Geotrichum eriense, Metschnikowia bicuspidata, Pachysolen tannophilus, Pichia membranaefaciens, Rhodotorula acheniorum, Geotrichum fermentans, Trichosporon cutaneum, Botryoascus synnaedendrus.*

More preferred as the above-mentioned microorganisms are, for example, the following strains:

*Candida etchellsii* IFO 1229, *Candida gropengiesseri* IFO 0659, *Candida halophila* IFO 1941, *Candida lactis-condensi* IFO 1286, *Candida mannitofaciens* IFO 1908, *Candida nodaensis* IFO 1942, *Candida parapsilosis* IFO 0585,

*Candida sorbophila* IFO 1583, *Candida tropicalis* IFO 0006, *Candida versatilis* IFO 1228, *Geotrichum candidum* CBS 187.67, *Geotrichum eriense* ATCC 22311.

*Metschnikowia bicuspidata* IFO 1408, *Pachysolen tannophilus* IFO 1007, *Pichia membranaefaciens* IAM 4258, *Rhodotorula acheniorum* IFO 10052, *Geotrichum fermentans* CBS 2529, *Trichosporon cutaneum* CBS 2466, *Botryoascus synnaedendrus* IFO 1604.

Suited for stereoselective asymmetric reduction of a (3S)-1-halo-3-amino-4-phenyl-2-butanone derivative to the corresponding (2R,3S)-1-halo-3-amino-4-phenyl-2-butanol derivative are, for example, the following microorganisms:

*Candida cantarellii* IFO 1261, *Candida fructus* IFO 1581, *Candida glabrata* IFO 0005, *Candida guilliermondii* IFO 0454, *Candida holmii* IFO 0660, *Candida intermedia* IFO 0761, *Candida maris* IFO 10003, *Candida melinii* IFO 0747, *Candida mogii* IFO 0436.

*Candida musae* IFO 1582, *Candida pintolopesii* var. *pintolopesii* IFO 0729, *Candida pintolopesii* var. *pintolopesii* IFO 0873, *Candida sonorensis* IFO 10027, *Cryptococcus albidus* IFO 0378, *Cryptococcus laurentii* IFO 0609.

*Citeromyces matritensis* IFO 0651, *Debaryomyces hansenii* var. *fabryi* IFO 0015, *Debaryomyces marama* IFO 0668, *Pichia anomala* IFO 0707.

*Pichia anomala* var. *miso* IFO 0144, *Pichia capsulata* IFO 0721, *Hansenula glucozyma* IFO 1472, *Pichia minuta* var. *minuta* IFO 0975, *Pichia minuta* var. *nonfermentans* IFO 1473, *Williopsis suaveolens* IFO 0809.

*Kloeckera corticis* IFO 0633, *Pichia toletana* IFO 0950, *Lipomyces starkeyi* IFO 0678, *Rhodosporidium sphaerocarpum* IFO 1438, *Rhodosporidium diobovatum* IFO 0688, *Rhodotorula glutinis* IFO 0395, *Rhodotorula glutinis* IFO 1099.

*Saccharomycopsis malanga* IFO 1710, *Wingea robertsii* IFO 1277.

IFO is the abbreviation for Institute for Fermentation, Osaka 17-85, Juso-honmachi 2-chome, Yodogawa-ku, Osaka 532, Japan. CBS is the abbreviation for Centraalbureau Voor Schimmelcultures, Oosterstraat 1, Postbus 273, NL-3740 AG Baarn, Netherlands. ATCC is the abbreviation for American Type Culture Collection, 12301 Parklawn Drive, Rockville, Md. 20852-1776.

Any nutrient source assimilable by these microorganisms can generally be used for the cultivation thereof. Thus, for example, there may be mentioned those ordinary media in which carbon sources, for example, carbohydrates such as glucose, sucrose, etc.; alcohols such as ethanol and glycerol, etc.; hydrocarbons such as paraffin etc.; organic acids such as acetic acid, propionic acid, etc.; soybean oil and the like, or the mixture of these; yeast extract, peptone, meat extract, corn steep liquor, nitrogen-containing inorganic nutrients such as ammonium sulfate, ammonia, etc.; and vitamins such as biotin, thiamine, etc. are incorporated in appropriate amounts.

These microorganisms can be cultivated, for example, under aerobic conditions in the nutrient medium pH range of 4.0 to 9.5 and the temperature range of 20° to 40° C. for 1 to 7 days.

In accordance with the present invention, optically active 1-halo-3-amino-4-phenyl-2-butanone derivatives can be stereoselectively reduced using the microorganisms mentioned above.

As the method of carrying out the above reduction, there may be mentioned, for instance, the method using the culture fluid as such, and the method comprising isolating microbial cells by centrifugation, for instance, resuspending the cells in phosphate buffer, water or the like, adding an amino-protected optically active 1-halo-3-amino-4-phenyl-2-butanone derivative and allowing the reaction to proceed.

In carrying out the above reaction, carbon sources such as glucose, sucrose, etc. may be added as energy sources. The cells may be used as such live cells or after such treatment as acetone treatment or lyophilization. The cells may be immobilized on a carrier or support prior to use.

The amino-protected optically active 1-halo-3-amino-4-phenyl-2-butanone derivatives may be added either as such or in the form of a solution in an organic solvent inert to the reaction, either all at once at the time of starting the reaction or in two or more portions during the reaction period. The above reduction reaction can be carried out with stirring within the pH range of 4 to 9 at a temperature of 10° to 60° C. for 3 to 120 hours.

The optically active 1-halo-3-amino-4-phenyl-2-butanol derivative formed by the reaction can be recovered by extracting the same, either directly from the reaction mixture or after separation of cells, with a solvent such as methanol, ethyl acetate, dichloromethane, etc., and, after dehydration, causing the same to crystallize out either directly or after purification by silica gel column chromatography, for instance.

The chemical purity and optical purity of the thus-obtained optically active 1-halo-3-amino-4-phenyl-2-butanol derivative can be determined in the same manner as mentioned hereinbefore by high-performance liquid chromatography using the Develosil HG3 column and methanol-water (4/6) eluent.

BEST MODES FOR CARRYING OUT THE INVENTION

The following examples are further illustrative of the present invention but are by no means limitative of the scope thereof.

EXAMPLE 1

Production of a (2S,3S)-1-chloro-3-methoxycarbonylamino-4-phenyl-2-butanol derivative A medium (medium ①) having the composition: 40 g of glucose, 3 g of yeast extract, 6.5 g of $(NH_4)_2HPO_4$, 1.0 g of $KH_2PO_4$, 0.8 g of $MgSO_4 \cdot 7H_2O$, 60 mg of $ZnSO_4 \cdot 7H_2O$, 90 mg of $FeSO_4 \cdot 7H_2O$, 5 mg of $CuSO_4 \cdot 5H_2O$, 10 mg of $MnSO_4 \cdot 4H_2O$ and 0.1 g of NaCl (per liter) was distributed in 5-ml portions into test tubes and, after sterilization, inoculated with the microorganisms shown in Table 1, Table 2, Table 3 and Table 4, followed by 2 to 3 days of shake culture under aerobic conditions at 30° C. (seed cultures).

In a 500-ml Sakaguchi flask were placed 27 ml of a medium (medium ②) having the composition: 3 g of yeast extract, 6.5 g of $(NH_4)_2HPO_4$, 1.0 g of $KH_2PO_4$, 0.8 g of $MgSO_4 \cdot 7H_2O$, 60 mg of $ZnSO_4 \cdot 7H_2O$, 90 mg of $FeSO_4 \cdot 7H_2O$, 5 mg of $CuSO_4 \cdot 5H_2O$, 10 mg of $MnSO_4 \cdot 4H_2O$, 0.1 g of NaCl and 5 g of $CaCO_3$ (per 900 ml) and one drop of Adekanol, followed by sterilization. After addition thereto of 3 ml of 40% glucose sterilized beforehand, 0.6 ml of each of the seed cultures mentioned above was inoculated and shake culture under aerobic conditions was carried out at 30° C. for 2 to 3 days. This culture fluid was adjusted to pH 6 with an aqueous sodium hydroxide or sulfuric acid solution. A 10-ml portion of said fluid, 400 mg of glucose and 10 mg of (3S)-1-chloro-3-methoxycarbonylamino-4-phenyl-2-butanone were placed in a 500-ml Sakaguchi flask and the mixture was shaken at 30° C. for 1 day to thereby allow the reaction to proceed.

Methanol was added directly to the reaction mixture for extracting (2S,3S)-1-chloro-3-methoxycarbonylamino-4-phenyl-2-butanol and, after addition of methanol to the marked line in a 50-ml volumetric flask, the conversion rate and stereoselectivity were determined by analyzing by high-performance liquid chromatography. The results obtained in this manner are shown in Table 1, Table 2, Table 3 and Table 4.

TABLE 1

| Microorganism | 2S,3S-Yield % | Selectivity 2S,3S/2R,3S |
| --- | --- | --- |
| Candida etchellsii I F O 1229 | 26.7 | About 90/10 |
| Candida gropengiesseri I F O 0659 | 86.8 | 99/1 |
| Candida halophila I F O 1941 | 15.5 | 84/16 |
| Candida lactis-condensi I F O 1286 | 45.8 | 93/7 |
| Candida mannitofaciens I F O 1908 | 17.1 | 85/15 |
| Candida nodaensis I F O 19429 | 41.7 | 88/12 |
| Candida parapsilosis I F O 0585 | 42.7 | 93/7 |
| Candida sorbophila I F O 15839 | 68.8 | 85/15 |
| Candida tropicalis I F O 00069 | 67.2 | About 97/3 |
| Candida versatilis I F O 1228 | 62.3 | 94/6 |
| Geotrichum candidum C B S 187, 67 | 49.9 | 92/8 |
| Geotrichum eriense A T C C 22311 | 53.4 | 96/4 |

TABLE 2

| Microorganism | 2S,3S-Yield % | Selectivity 2S,3S/2R,3S |
| --- | --- | --- |
| Metchnikowia bicuspidata I F O 1408 | 49.9 | 87/13 |
| Pachysolen tannophilus I F O 1007 | 69.7 | 93/7 |
| Pichia membranaefaciens I AM 4258 | 27.5 | 81/19 |
| Rhodotorula acheniorum I F O 10052 | 25.4 | About 99/1 |
| Geotrichum fermentans C B S 2529 | 72.5 | 96/4 |
| Trichosporon cutaneum C B S 2466 | 53.1 | 93/7 |
| Botryoascus synnaedendrus I F O 1604 | 18.5 | About 86/14 |

TABLE 3

| Microorganism | 2R,3S-Yield % | Selectivity 2S,3S/2R,3S |
| --- | --- | --- |
| Candida cantarellii I F O 1261 | 67.7 | 12/88 |
| Candida fructus I F O 1581 | 79.9 | 2/98 |
| Candida glabrata I F O 0005 | 69.0 | 3/97 |
| Candida guilliermondii I F O 0454 | 53.3 | 19/81 |
| Candida holmii I F O 0660 | 81.5 | 2/98 |
| Candida intermedia I F O 0761 | 74.0 | 4/96 |
| Candida maris I F O 10003 | 70.5 | 1/99 |
| Candida melinii I F O 0747 | 76.5 | 16/84 |
| Candida mogii I F O 0436 | 71.7 | 7/93 |
| Candida musea I F O 1582 | 76.1 | 1/99 |
| Candida pintoropesii var. pintropesii I F O 0729 | 82.7 | 1/99 |
| Candida pintoropesii var. pintropesii I F O 0873 | 79.5 | 2/98 |
| Candida sonorensis I F O 10027 | 89.7 | 1/99 |
| Cryptococcus laurentii I F O 0609 | 51.7 | 3/97 |
| Citeromyces matritensis I F O 0651 | 61.4 | 3/97 |
| Debaryomyces hansenii var. fabryi I F O 0015 | 59.0 | 1/99 |
| Debaryomyces marama I F O 0668 | 73.9 | 3/97 |
| Pichia anomala I F O 0707 | 76.3 | 14/86 |
| Pichia anomala I F O 0141 | 69.9 | 12/88 |
| Pichia capsulata I F O 0721 | About 100 | 4/96 |

TABLE 4

| Microorganism | 2R,3S- Yield % | Selectivity 2S,3S/2R,3S |
|---|---|---|
| Pichia glucozyma I F O 1472 | 76.0 | 3/97 |
| Pichia minuta var. minuta | 78.4 | 7/93 |
| Pichia minuta var. nonfermentans I F O 1473 | 73.4 | 9/91 |
| Williopsis suaveolens I F O 0809 | 73.5 | 5/95 |
| Hansenula sp. | 62.1 | 16/84 |
| Kloeckera corticis I F O 0633 | 23.3 | 19/81 |
| Pichia toletana I F O 0950 | 58.5 | 1/99 |
| Lipomyces starkeyi I F O 0678 | 24.9 | 3/97 |
| Rhodsporidium sphaerocarpum I F O 1438 | 46.1 | 0/100 |
| Rhodsporidium diobovatum I F O 0688 | 39.2 | 13/87 |
| Rhodotorula glutinis I F O 0395 | 69.9 | 5/95 |
| Rhodotorula glutinis I F O 1099 | 48.6 | 14/86 |
| Saccharomycopsis malanga I F O 1710 | 84.6 | 2/98 |
| Wingea robertsii I F O 1277 | 79.7 | 1/99 |

EXAMPLE 2

Production of (2S,3S)-1-chloro-3-methoxycarbonylamino-4-phenyl-2-butanol

A culture was obtained by the same method as in Example 1 using *Geotrichum eriense* ATCC 22311 as the microorganism and then adjusted to pH 6 with an aqueous sodium hydroxide solution and an aqueous sulfuric acid solution. A 25-ml portion of this culture, 1 g of glucose and (3S)-1-chloro-3-methoxycarbonylamino-4-phenyl-2-butanone were mixed up in a 500-ml Sakaguchi flask and the mixture was shaken for 1 day to thereby allow the reaction to proceed. Then, again, 250 mg of (3S)-1-chloro-3-methoxycarbonylamino-4-phenyl-2-butanone was added. The reaction was allowed to proceed for further 2 days with shaking while the glucose concentration was controlled within the range of 0 to 4% by adding glucose portionwise. Thereafter, a further 250 mg portion of (3S)-1-chloro-3-methoxycarbonylamino-4-phenyl-2-butanone was added and shaking was continued for further 4 days to allow the reaction to proceed while controlling the glucose concentration in the same manner as mentioned above. The reaction mixture was diluted with 100 ml of water and extracted with 100 ml portion of ethyl acetate for 3 times. The organic extract layers were combined, washed with 100 ml of water and further with 100 ml of a saturated aqueous sodium chloride solution and then dried over anhydrous sodium sulfate. This solution was concentrated to dryness to give (2S,3S)-1-chloro-3-methoxycarbonylamino-4-phenyl-2-butanol as a white solid (607 mg; yield 67%; purity 83.7 wt %; selectivity 2S,3S/2R,3S=97/3; optical purity 99.7% ee).

EXAMPLE 3

Production of (2S,3S)-1-chloro-3-methoxycarbonylamino-4-phenyl-2-butanol

A culture was obtained by the same method as in Example 1 using *Candida gropengiesseri* IFO 0659 as the microorganism and adjusted to pH 6 with an aqueous sodium hydroxide solution and an aqueous sulfuric acid solution. A 75-ml portion of this culture was separated into a supernatant and cells by centrifugation. To the whole amount of the cells was added a portion of the supernatant to make the total volume 25 ml. This cell suspension (25 ml), 1 g of glucose and 250 mg of (3S)-1-chloro-3-methoxycarbonylamino-4-phenyl-2-butanone were mixed together in a 500-ml Sakaguchi flask and the mixture was shaken for 1 day to allow the reaction to proceed. A further 250-mg portion of (3S)-1-chloro-3-methoxycarbonylamino-4-phenyl-2-butanone was added. The reaction was allowed to proceed by shaking for further 6 days while controlling the glucose concentration within the range of 0 to 4% by adding glucose portionwise. Water, 100 ml, was added to the reaction mixture and the whole mixture was extracted with 100 ml portion of ethyl acetate for 3 times. The organic extract layers were combined, washed with 100 ml of water and further with 100 ml of a saturated aqueous sodium chloride solution and dried over anhydrous sodium sulfate. This solution was concentrated to dryness to give (2S,3S)-1-chloro-3-methoxycarbonylamino-4-phenyl-2-butanol as a white solid (401 mg; yield 61%; purity 76.8 wt %; selectivity 2S,3S/2R,3S=98/2; optical purity 98.3% ee).

INDUSTRIAL APPLICABILITY

According to the present invention, specific microorganisms are used to asymmetrically reduce optically active 1-halo-3-amino-4-phenyl-2-butanone derivatives, as mentioned above, hence optically active 1-halo-3-amino-4-phenyl-2-butanol derivatives can be obtained stereoselectively in high yields.

We claim:

1. A process for producing optically active 1-halo-3-amino-4-phenyl-2-butanol derivatives which comprises bringing an optically active 1-halo-3-amino-4-phenyl-2-butanone derivative of the formula (1)

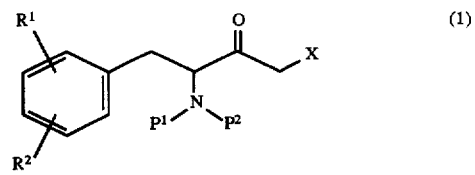

wherein X is a halogen atom, $R^1$ and $R^2$ each independently is a hydrogen atom, a hydroxyl group which is optionally protected, an alkoxyl group, an alkyl group, a nitro group, an amino group which is optionally protected, or a cyano group, $P^1$ and $P^2$ each independently is a hydrogen atom or an amino-protecting group or $P^1$ and $P^2$ combined are a phthaloyl group, with the exception of the case in which both $P^1$ and $P^2$ are simultaneously hydrogen atoms, into contact with at least one microorganism selected from the group consisting of microorganisms belonging to the genera Candida, Geotrichum, Metschnikowia, Pachysolen, Pichia, Rhodotorula, Trichosporon, Zygosaccharomyces, Botryoascus, Cryptococcus, Citeromyces, Debaryomyces, Williopsis, Kloeckera, Lipomyces, Rhodosporidium, Saccharomycopsis and Wingea and capable of stereoselectively reducing said butanone derivative to the corresponding optically active 1-halo-3-amino-4-phenyl-2-butanol derivative of the formula (2).

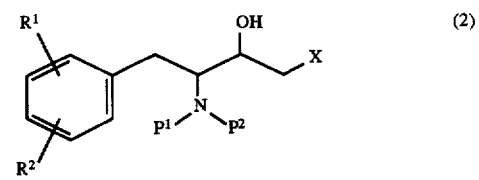

wherein X, $R^1$, $R^2$, $P^1$ and $P^2$ are as defined above, and recovering the resulting optically active 1-halo-3-amino-4-phenyl-2-butanol derivative.

2. The process for producing optically active 1-halo-3-amino-4-phenyl-2-butanol derivatives according to claim 1, wherein said optically active 1-halo-3-amino-4-phenyl-2- butanone derivative is a (3S)-1-halo-3-amino-4-phenyl-2-butanone derivative, said optically active 1-halo-3-amino-4-phenyl-2-butanol derivative is a (2S,3S)-1-halo-3-amino-4-phenyl-2-butanol derivative, and said microorganism is at least one microorganism selected from the group consisting of microorganisms belonging to the genera Candida, Geotriochum, Metschnikowia, Pachysolen, Pichia, Rhodotorula, Trichosporon and Botryoascus.

3. The process for producing optically active 1-halo-3-amino-4-phenyl-2-butanol derivatives according to claim 2, wherein said microorganism is *Candida etchellsii, Candida gropengiesseri, Candida halophila, Candida lactiscondensi, Candida mannitofaciens, Candida nodaensis, Candida parapsilosis, Candida sorbophila, Candida tropicalis, Candida versatilis, Geotrichum candidum, Geotrichum eriense, Metschnikowia bicuspidata, Pachysolen tannophilus, Pichia membranaefaciens, Rhodotorula acheniorum, Geotrichum fermentans, Trichosporon cutaneum,* or *Botryoascus synnaedendrus.*

4. The process for producing optically active 1-halo-3-amino-4-phenyl-2-butanol derivatives according to claim 2, wherein said optically active 1-halo-3-amino-4-phenyl-2-butanone derivative is (3 S)- 1 -chloro-3 -methoxycarbonylamino-4-phenyl-2-butanone, (3 S)- 1 -chloro-3-t-butoxycarbonylamino-4-phenyl-2-butanone, (3S)-1-chloro-3-benzyloxycarbonylamino-4-phenyl-2-butanone or (3 S)- 1 -chloro-3 -phthaloylamino-4-phenyl-2-butanone.

5. The process for producing optically active 1-halo-3-amino-4-phenyl-2-butanol derivatives according to claim 1, wherein said microorganism is *Candida etchellsii, Candida gropengiesseri, Candida halophila, Candida lactiscondensi, Candida mannitofaciens, Candida nodaensis, Candida parapsilosis, Candida sorbophila, Candida tropicalis, Candida versatilis, Geotrichum candidum, Geotrichum eriense, Metschnikowia bicuspidata, Pachysolen tannophilus, Pichia membranaefaciens, Rhodotorula acheniorum, Geotrichum fermentans, Trichosporon cutaneum,* or *Botryoascus synnaedendrus.*

6. The process for producing optically active 1-halo-3-amino-4-phenyl-2-butanol derivatives according to claim 5, wherein said optically active 1-halo-3-amino-4-phenyl-2-butanone derivative is (3 S)- 1 -chloro-3 -methoxycarbonylamino-4-phenyl-2-butanone, (3 S)- 1 -chloro-3-t-butoxycarbonylamino-4-phenyl-2-butanone, (3S)-1-chloro-3-benzyloxycarbonylamino-4-phenyl-2-butanone or (3S)-1-chloro-3-phthaloylamino-4-phenyl-2-butanone.

7. The process for producing optically active 1-halo-3-amino-4-phenyl-2-butanol derivatives according to claim 1, wherein said optically active 1-halo-3-amino-4-phenyl-2-butanone derivative is (3S)-1-chloro-3-methoxycarbonylamino-4-phenyl-2-butanone, (3S)-1-chloro-3-t-butoxycarbonylamino-4-phenyl-2-butanone, (3S)-1-chloro-3-benzyloxycarbonylamino-4-phenyl-2-butanone or (3S)-1-chloro-3-phthaloylamino-4-phenyl-2-butanone.

8. The process for producing optically active 1-halo-3-amino-4-phenyl-2-butanol derivatives according to claim 1, wherein said optically active 1-halo-3-amino-4-phenyl-2-butanone derivative is a (3S)-1-halo-3-amino-4-phenyl-2-butanone derivative, said optically active 1-halo-3-amino-4-phenyl-2- butanol derivative is a (2S,3S)-1-halo-3-amino-4-phenyl-2-butanol derivative, and said microorganism is *Candida etchellsii* IFO 1229, *Candida gropengiesseri* IFO 0659, *Candida halophila* IFO 1941, *Candida lactiscondensi* IFO 1286, *Candida mannitofaciens* IFO 1908, *Candida nodaensis* IFO 1942, *Candida parapsilosis* IFO 0585, *Candida sorbophila* IFO 1583, *Candida tropicalis* IFO 0006, *Candida versatilis* IFO 1228, *Geotrichum candidum* CBS 187,67, *Geotrichum eriense* ATCC 22311, *Metschnikowia bicuspidata* IFO 1408, *Pachysolen tannophilus* IFO 1007, *Pichia membranaefaciens* IAM 4258, *Rhodotorula acheniorum* IFO 10052, *Geotrichum fermentans* CBS 2529, *Trichosporon cutaneum* CBS 2466, or *Botryoascus synnaedendrus* IFO 1604.

9. The process for producing optically active 1-halo-3-amino-4-phenyl-2-butanol derivatives according to claim 1, wherein said optically active 1-halo-3-amino-4-phenyl-2-butanone derivative is a (3S)-1-halo-3-amino-4-phenyl-2-butanone derivative, said optically active 1-halo-3-amino-4-phenyl-2-butanol derivative is a (2R,3S)-1-halo-3-amino-4-phenyl-2-butanol derivative, and said microorganism is at least one microorganism selected from the group consisting of microorganisms belonging to the genera Candida, Cryptococcus, Citeromyces, Debaryomyces, Pichia, Williopsis, Kloeckera, Lipomyces, Rhodosporidium, Rhodotorula, Saccharomycopsis and Wingea.

10. The process for producing optically active 1-halo-3-amino-4-phenyl-2-butanol derivatives according to claim 9, wherein said optically active 1-halo-3-amino-4-phenyl-2-butanone derivative is a (3 S)-1-halo-3-amino-4-phenyl-2-butanone derivative, said optically active 1-halo-3-amino-4-phenyl-2-butanol derivative is a (2R, 3S)-1-halo-3-amino-4-phenyl-2-butanol derivative, and said microorganism is *Candida cantarellii* IFO 1261, *Candida fructus* IFO 1581, *Candida glabrata* IFO 0005, *Candida guilliermondii* IFO 0454, *Candida holmii* IFO 0660, *Candida intermedia* IFO 0761, *Candida maris* IFO 10003, *Candida melinii* IFO 0747, *Candida mogii* IFO 0436, *Candida musae* IFO 1582, *Candida pintolopesii* var. *pintolopesii* IFO 0729, *Candida pintolopesii* var. *pintolopesii* IFO 0873, *Candida sonorensis* IFO 10027, *Cryptococcus albidus* IFO 0378, *Cryptococcus laurentii* IFO 0609, *Citeromyces matritensis* IFO 0651, *Debaryomyces hansenii* var. *fabryi* IFO 0015, *Debaryomyces marama* IFO 0668, *Pichia anomala* IFO 0707, *Pichia anomala* IFO 0141, *Pichia capsulata* IFO 0721, *Hansenula glucozyma* IFO 1472, *Pichia minuta* var. *minuta* IFO 0975, *Pichia minuta* var. *nonfermentans* IFO 1473, *Williopsis suaveolens* IFO 0809, *Kloeckera Corticis* IFO 0633, *Pinchia toletana* IFO 0950, *Lipomyces starkeyi* IFO 0678, *Rhodosporidium sphaerocarpum* IFO 1438, *Rhodosporidium diobovatum* IFO 0688, *Rhodotorula glutinis* IFO 0395, *Rhodotorula glutinis* IFO 1099, *Saccharomycopsis malanga* IFO 1710, or *Wingea robertsii* IFO 1277.

11. The process for producing optically active 1-halo-3-amino-4-phenyl-2-butanol derivatives according to claim 1 wherein said optically active 1-halo-3-amino-4-phenyl-2-butanone derivative is a (3S)-1-halo-3-amino-4-phenyl-2-butanone derivative, said optically active 1-halo-3-amino-4-phenyl-2-butanol derivative is a (2R,3S)-1-halo-3-amino-4-phenyl-2-butanol derivative, and said microorganism is *Candida cantarellii* IFO 1261, *Candida fructus* IFO 1581, *Candida glabrata* IFO 0005, *Candida guilliermondii* IFO 0454, *Candida holmii* IFO 0660, *Candida intermedia* IFO 0761, *Candida maris* IFO 10003, *Candida melinii* IFO 0747, *Candida mogii* IFO 0436, *Candida musae* IFO 1582, *Candida pintolopesii* var. *pintolopesii* IFO 0729, *Candida pintolopesii* var. *pintolopesii* IFO 0873, *Candida sonorensis* IFO 10027, *Cryptococcus albidus* IFO 0378, *Cryptococcus laurentii* IFO 0609, *Citeromyces matritensis* IFO 0651, *Debaryomyces hansenii* var. *fabryi* IFO 0015, *Debaryomyces marama* IFO 0668, *Pichia anomala* IFO 0707, *Pichia anomala* IFO 0141, *Pichia capsulata* IFO 0721, *Hansenula glucozyma* IFO 1472, *Pichia minuta* var. *minuta* IFO 0975,

*Pichia minuta* var. *nonfermentans* IFO 1473, *Williopsis suaveolens* IFO 0809, *Kloeckera corticis* IFO 0633, *Pichia toletana* IFO 0950, *Lipomyces starkeyi* IFO 0678, *Rhodosporidium sphaerocarpum* IFO 1438, *Rhodosporidium diobovatum* IFO 0688, *Rhodotorula glutinis* IFO 0395, *Rhodotorula glutinis* IFO 1099, *Saccharomycopsis malanga* IFO 1710, or *Wingea robertsii* IFO 1277.

* * * * *